United States Patent [19]

Lim

[11] 4,257,884
[45] Mar. 24, 1981

[54] CHROMATOGRAPHY

[75] Inventor: Franklin Lim, Richmond, Va.

[73] Assignee: Damon Corporation, Needham Heights, Mass.

[21] Appl. No.: 30,848

[22] Filed: Apr. 17, 1979

[51] Int. Cl.³ .............................................. B01D 15/08
[52] U.S. Cl. .................................... 210/656; 210/502; 210/198.2; 55/67; 252/316; 435/288; 435/182; 23/230 B; 424/1.5
[58] Field of Search ................. 210/31 C, 198 C, 502; 55/67, 386; 252/316; 435/815, 196, 288; 23/230 B; 424/1.5

[56] References Cited

U.S. PATENT DOCUMENTS

| | | | |
|---|---|---|---|
| 3,471,261 | 10/1969 | Patterson | 210/31 C |
| 3,859,228 | 1/1975 | Morishita et al. | 252/316 |
| 3,947,352 | 3/1975 | Cuatrecasas et al. | 210/31 C |
| 3,985,840 | 10/1975 | Hofacker | 252/316 |
| 4,143,201 | 3/1979 | Miyashiro et al. | 210/31 C |

OTHER PUBLICATIONS

"The Microencapsulation of Hemoglobin Solutions: Techniques of Production and Characterization," R. D. Moss, PHD Thesis, May 1975.

Primary Examiner—Ivars C. Cintins
Assistant Examiner—E. Rollins Cross
Attorney, Agent, or Firm—Kenway & Jenney

[57] ABSTRACT

Semipermeable microcapsules are employed as a medium to chromatographically separate mixtures of solutes. The microcapsules comprise membranes having a selected upper limit of permeability and contain a filler material capable of maintaining the membranes in a distended position. In use, the capsules are packed in a column and equilibrated with the solvent of the mixture to be separated. Components in the mixture are separated when passed through the column on the basis of their molecular diameter. The material is well suited for resolving components of a mixture of solutes in the 100–5000 molecular weight range.

In another embodiment, a specific binding substance such as an antibody is confined within capsule membranes permeable to the antibody's complementary antigen to produce a material useful in affinity chromatography.

12 Claims, 2 Drawing Figures

CHROMATOGRAPHY

BACKGROUND OF THE INVENTION

This invention relates to chromatographic separation techniques and to materials useful in such techniques. More particularly, it relates to the chromatographic use of semipermeable microcapsules.

Chromatography procedures are used to separate the components of a mixture of solutes. Basically, they involve the flow of a mobile phase of gas or liquid containing a mixture of solutes over a stationary phase. As the mobile phase moves past the stationary phase, repeated sorption and desorption of the solutes occur at rates determined, among other factors, by each solute's ratio of distribution between the phases. The solutes in the mixture thus move at different rates along the chromatographic flow path, producing a characteristic pattern of zones rich in individual solutes called a chromatogram. Usually, the separate fractions are eluted from the flow path for identification or other purposes.

Zeolites, and certain cross-linked polysaccharides, polystyrenes, polyacrylamides, and agarose gels are employed in a type of chromatography known as gel filtration. These substances are often referred to as "molecular sieves". All are characterized by an open structure through which solutes of various critical diameter pass at different rates. When packed in a column, these materials effectively separate the components of a mixture of solutes on the basis of their critical diameter. Prior to use, these materials must be swelled by immersion in a solvent, usually water, for a time sufficient to establish equilibrium and to stabilize pore size. Cross-linked polyacrylamide and polysaccharide gels are capable of resolving solutes over a wide molecular weight range, up to about 200,000 for polysaccharides, and up to about 800,000 for proteins. Agarose gels separate mixtures containing molecules in a molecular weight range of approximately $0.5 \times 10^5$ to $150 \times 10^6$. Zeolites separate materials in the molecular weight range below about 200 daltons.

The cross-linked polymeric materials discussed above are only marginally effective as molecular sieves for separating substances of molecular weight in the range below about 1000–2000 daltons, and the zeolites are unsuitable for resolving solutes of molecular weight above about 200 daltons.

Recently, another separation technique known as affinity chromatography has been developed. Affinity chromatography involves immobilizing on a suitable support one component of a two-component specific binding complementary pair such as the antibody of an antibody-antigen pair or the hormone binding protein of a binding protein-hormone pair. The immobilized component is then packed into a column. On passage of a mixture of materials, one component of which comprises the immobilized substance's complementary binding components, the complementary component is selectively extracted. The resulting bond can be broken with a suitable reagent such as an acid solution or a solution of high salt concentration, and the concentrated component can be recovered. This technique has found utility in various research efforts and in the purification of complex proteins.

In a related technique enzyme is immobilized on a substrate and packed into a column for use as a reusable enzyme reactor. Solutions containing the enzyme's substrate or substrate system may then be passed through the system and chemically changed by the catalytic influence of the enzyme.

SUMMARY OF THE INVENTION

It has now been discovered that chromatographic separation columns may be made using semipermeable microcapsules as the chromatographic separation material. Specifically, it has been observed that semipermeable microcapsules when packed into a column or otherwise arranged within means defining a flow path, can serve as a chromatographic medium effective to separate mixtures of molecules having molecular weights within the permeability range of the membranes. Advantageously, such microcapsules are well suited for resolving components varying in molecular weight between about 100 to 5000 daltons.

The membranes which form the microcapsules are believed to have a structure defining pores into which solutes of different molecular diameter diffuse at different rates. If microcapsules containing a filler material capable of preventing collapse of the membranes are packed within means defining a flow path such as a column, and a solution of mixed solutes is passed therethrough, components of the mixture having molecular weights within the range of permeability of the membranes interact with the capsule to varying degrees and are separated into a chromatogram, zones of which are rich in subsets of solutes making up the mixture. Solutes of a molecular weight in excess of the permeability of the microcapsules pass through the column without substantial interaction. When used in this way, the filler material within the capsules is preferably a high molecular weight hydrophilic material such as albumin, a polyvinyl pryrrolidone, a polyethylene glycol, a polysaccharide, albumin or the like, and prior to use, the capsules are equilibrated with the solvent of the mixture to be separated.

In another aspect of the invention, the higher molecular weight component of a pair of complementary components capable of specific binding is encapsulated in a membrane having a permeability insufficient to allow diffusion of the encapsulated component, but sufficient to allow free passage of its lower molecular weight, complementary component. This material is useful in affinity chromatography for selectively extracting a component from a complex mixture, and as an enzyme reactor for catalyzing specific chemical changes in specific substrates. The encapsulated material is immobilized, but none of its binding sites are occupied by bonds to a solid surface. Accordingly, the encapsulated component can react with its complementary component without steric hindrance.

Accordingly, it is an object of the invention to provide new materials for chromatographic use and new chromatography techniques. Another object of the invention is to provide a material capable of acting as a molecular sieve for solutes in the molecular weight range of 100 to 5000 daltons. These and other objects and features of the invention will be apparent from the following description of some preferred embodiments and from the drawing wherein various parts of the illustrations are exaggerated in size for clarity.

DESCRIPTION OF THE PREFERRED EMBODIMENT

At the heart of the invention is the discovery that semipermeable microcapsules may be used as a material for chromatographically separating components of a mixture of solutes in a liquid carrier. The success of the invention is dependent on the availability of microcapsules having a permeability sufficient to exclude the passage of materials above a given molecular weight level, but to allow diffusion of materials below that level.

Figure 1:
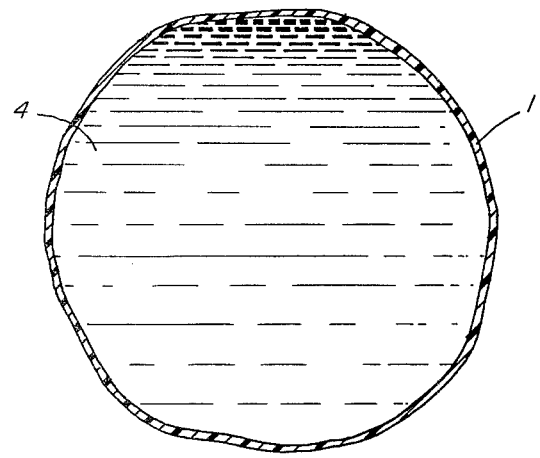
FIG. 1 is an enlarged, schematic cross-sectional view of a microcapsule useful in the process and apparatus of the invention.

A microcapsule useful in the techniques disclosed herein is schematically illustrated in FIG. 1. It comprises an enclosed, generally spheroidal semipermeable membrane 1 containing an aqueous liquid 4. The membrane 1 typically has a high tensile strength but is incapable of retaining its generally spheroidal form unless maintained in a distended position by an encapsulated water soluble or semisolid material which cannot diffuse across the membrane and which behaves as a filler. Preferably, the filler comprises an aqueous solution of a hydrophilic natural or synthetic polymer. Preferred filler materials include high molecular weight (e.g. 40,000 daltons or more) polyvinyl pyrrolidone, polysaccharides, polyethylene glycol, and albumin, but many other high molecular weight substances can be employed.

Techniques for producing uniformly permeable microcapsules which allow passage of solutes of molecular weight above a desired level are disclosed in detail in U.S. application Ser. Nos. 606,166, filed Aug. 20, 1975; 931,177, filed Aug. 4, 1978; and 030,847, filed on even date herewith, all to F. Lim et al., and in U.S. application Ser. No. 24,600, filed Mar. 29, 1979 to F. Lim. The techniques of the Ser. Nos. 606,166, 931,177 and 847 applications involve a modification of the known interfacial polymerization encapsulation process which allows one to exert significantly improved control over the quality, uniformity, and permeability of capsule membranes. Briefly, a pair of mutually immisible solvents or solvent systems are selected, and one monomer of a complementary pair which form a copolymer is dissolved in one of the solvents together with the material to be encapsulated. The solvent containing the material to be encapsulated is then emulsified within the other solvent to form a plurality of discrete droplets. The second, complementary monomer is next added to the continuous phase of the emulsion to initiate polymerization about the droplets at the phase boundary. Membrane permeability and uniformity of polymer deposition are controlled by varying the affinity of the continuous phase of the emulsion for the encapsulated monomer during the course of polymerization and by controlling the concentration of the reacting monomers and the duration of the polymerization.

In one approach, the continuous phase at the outset is a solvent or solvent system having a relatively high affinity for the encapsulated monomer so that, in a first stage of polymerization, a relatively thick polymer network is produced about the droplets. Thereafter, the continuous phase is altered such that its affinity for the first monomer is decreased, e.g., by diluting the continuous phase with a second solvent or by replacing the continuous phase with a fresh solvent. Upon the addition of second monomer, further polymerization occurs preferentially within the initially deposited polymer network, patching macroporous defects and resulting in uniform capsule membranes which allow diffusion of solutes below a certain molecular weight.

In another approach, the continuous phase at the outset is selected to have a low affinity for the encapsulated monomer so that thin, relatively dense membranes form in a first stage of polymerization. Thereafter, the affinity of the continuous phase for the encapsulated monomer is increased to draw further quantitites of monomer through the membrane and to deposit a second outer layer of insoluble polymer.

If the discontinuous droplet phase is aqueous, and is buffered to provide a compatible environment for labile biological materials such as an antibody or an enzyme, the encapsulation can be conducted in a manner to preserve a large percentage of the labile material's biological activity. The operability of the encapsulated material is also preserved by adding second monomer to the continuous phase in increments over the duration of the polymerization so that its concentration at any given time is relatively low and the antibody, etc. is not exposed to high concentrations of potentially destructive substances.

In a preferred reaction system, aqueous droplets containing a diamine and a filler material are produced in a continuous phase of cyclohexane whose affinity for the monomer dissolved in the droplet phase is modified by the addition of chloroform as a diluent. The addition of a diacid halide to the system results in the formation of semipermeable polyamide microcapsules. This microencapsulation approach is effective for producing membranes having an upper limit of permeability in the 2000–30,000 dalton molecular weight range.

The 24,600 application discloses a technique for producing semipermeable microcapsules containing living tissue. However, it is well-suited for encapsulating many other materials, and allows one to control permeability with considerable precision. In accordance with the procedure disclosed in the 24,600 application, the material to be encapsulated is dissolved or suspended in an aqueous solution of a water-soluble gum, gelatin, or agar, of the type which can be reversibly transformed into a shape retaining mass by exposure to multivalent ions or solutions of a selected pH (in the case of the gums) or a temperature change (in the case of gelatin and agar). Thereafter, the liquid solution is formed into droplets and gelled to form discrete, shape-retaining, typically spherical or spheroidal "temporary" capsules. This step can be accomplished, for example, by extruding the water-gum-core material mixture from a vibrating capillary located in the center of a vortex created by rapidly stirring a calcium chloride solution. Droplets of the mixture are thrown from the tip of the capillary into the calcium ion solution where the gum is rapidly crosslinked by the divalent calcium ions to result in shape-retaining, spheroidal-shaped masses of gel.

In the next step of the process, a semipermeable membrane is deposited in a surface layer of the temporary capsules. This can be done by immersing the capsules in a dilute solution of a polymer containing groups reactive with functionalities in the gel molecules. For example, when the temporary capsule comprises an acidic, polysaccharide gum, polymers containing acid reactive groups such as polyethyleneimine or polylysine can be used. In this situation, the polysaccharide is permanently crosslinked in an outer layer by reaction between its carboxyl groups and the amine groups.

The permeability of the resulting cross-linked membrane can be controlled by selecting the molecular weight of the crosslinking polymer used. A solution of polymer having a low molecular weight, in a given time period, penetrates further into the temporary capsules than a higher molecular weight polymer. The degree of penetration of the crosslinker has been correlated with the resulting permeability. In general, the higher the molecular weight of the crosslinking polymer, the less it penetrates the gel and the greater is the upper limit of permeability. Polymers of low molecular weight penetrate deeper, resulting in a thick, far less porous membrane, permeable only to materials of lower molecular weight. Broadly, polymers within the molecular weight range of 3,000 to 100,000 daltons or greater may be used, depending on the duration of the reaction, the concentration of the polymer solution, and the degree of porosity desired. One successful set of reaction conditions, using polylysine of average molecular weight of about 35,000 daltons involved reaction for two minutes, with stirring, of a saline solution containing 0.167 percent polylysine. This treatment resulted in membranes having an upper permeability limit of about 70,000 daltons. Optimal reaction conditions suitable for controlling permeability in a given system can readily be determined empirically without the exercise of invention.

Lastly, the gel is reliquified to its water soluble form. This may be done by re-establishing the conditions under which the gum is a liquid, e.g., changing the pH of the medium or removing the calcium or other multifuctional cations used. In the gels which are insoluble in the presence of multivalent cations, the medium in the capsule can be resolubilized simply by immersing the capsules in a solution which contains alkali metal ions and hydrogen ions. Monovalent ions exchange with the calcium or other multifunctional ions within the gum when the capsules are immersed in the solution with stirring. It is often also desirable to treat the capsules so as to tie up free amino groups or the like which would otherwise impart to the capsules a tendency to clump. This can be done, for example, by immersing the capsules in a solution of sodium alginate.

The ability of microcapsules of the type described to separate solutes of different molecular weights (more precisely different critical diameters) is dependent on the permeability of the membranes. It is believed that the membranes consist of a polymer framework having voids of varying diameter, some of which define a tortuous path to the interior of the microcapsule. When a water-soluble or water dispersible filler material of molecular weight in excess of the upper permeability limit is included in the microcapsules, they attain some structural strength and can be packed in a column without seriously restricting flow. Preferably, prior to use, the capsules are equilibrated with the solvent of the mixture to be separated so as to stabilize the dimensions of voids within the membrane. The material is then introduced into a column 10 (see FIG. 2), fitted with a bed support 12 and a valve 14. Because the capsules may be quite small (e.g. 20-100 microns in diameter) they have a high surface area to volume ratio and a high activity. They should not be stacked to a height wherein membranes compact and clog the column.

In operation, a mixture of solutions of varying molecular weight is passed along the column flow path 16. Solutes in the mixture having a critical diameter above the upper permeability limit of the microcapsules pass through the column substantially without interaction, and on elution appear in the void volume. Solutes having a molecular diameter within the permeability range of the microcapsules interact with them at different rates by repeated excursions into and out of the permeable polymer framework of the capsule membranes. Their passage along the flow path is selectively retarded, resulting in the formation of spaced-apart zones rich in solutes within a narrow molecular diameter range. Elution of these zones with a suitable solvent results in fractions such as depicted at 18, rich in respective solutes or a subset of solutes.

Microcapsules having an upper limit of permeability in the 25,000-30,000 dalton range may be used as a material for resolving components in a mixture in the 100 to 30,000 molecular weight range, and are well suited for resolving components in the 100-5000 molecular weight range. At the low end of this range, resolution may be achieved among solutes having a difference in molecular weight in the range of about 50 daltons or less.

In preparing a material for use in affinity chromatography, the higher molecular weight component of a pair of substances capable of specific binding, e.g., an antibody, is encapsulated within membranes readily permeable to the lower molecular weight component but impermeable to the encapsulated material. The antibody is in effect immobilized in the capsules, yet is not bound in the sense that a chemical bond is formed between the antibody and a support. If a mixture of solutes, one component of which is the lower molecular weight complementary component of the encapsulated substance, is then passed through a mass of such capsules, low molecular weight component associates with the encapsulated material, and the remainder of the solutes in the mixture pass through without binding. Thereafter, the antigen-antibody bond may be broken, e.g., by passing an acidic solution through the capsules. These capsules may be used in a column or other flow-through system. For example, antigen may be extracted from a mixed solution as capsules confined within a porous pouch or the like are soaked in the solution.

Microcapsules of this type may also be used as an enzyme reactor to catalyze a specific chemical change in the enzyme's substrate. Where one or more enzymes are encapsulated within membranes permeable to the substances which react with them, the resulting microcapsules may be used as an enzyme reactor. Microcapsules may be disposed within means defining a flow path and equilibrated with an aqueous solution of a pH suitable for promoting the catalytic change. A solution containing the substrate(s) is then passed along the flow path. Substrate molecules traverse the capsule membrane and are chemically changed by the enzyme. The product can then be eluted from the column.

Alternatively, the microcapsules may be dispersed in an aqueous solution of the substrate, preferably while stirring, for a sufficient amount of time to allow diffusion of substrate molecules and the resulting product across the membranes. The microcapsules are then isolated from the solution, e.g., by centrifugation, and the product is recovered. In still another alternative, microcapsules containing enzyme may be disposed within an enclosure permeable to dissolved substances but impermeable to the capsules themselves.

The outstanding advantages of such encapsulated enzymes is that they are easily separated from their environment, reactive, yet protected. Accordingly, a given enzyme reagent may be reused.

The invention will be further understood from the following nonlimiting examples.

EXAMPLE 1

Hexanediamine carbonate (pH=8.5±0.1) solution is prepared by mixing 17.7 ml 1,6 hexanediamine with 32 ml of water, and bubbling $CO_2$ through the solution for about 1 hour or until the pH level is reached. Terephthaloyl chloride (TCl) solution is prepared by adding 20 g TCl in 200 ml of organic solvent consisting of 4 parts cyclohexane and 1 part chloroform. TCl is dissolved by stirring vigorously, and the solution is then centrifuged for 10 minutes at 2600 rpm. Any precipitate is discarded.

750 ml cyclohexane are mixed with 125 ml SPAN-85 in a 2-liter mixer equipped with a magnetic stirring bar. While stirring, a mixed solution made from 25 ml of 15% polyvinylpyrrolidone-4% bovine serum albumin, 30 ml of hexanediamine carbonate solution is added to the cyclohexane. When droplets of the desired size have been produced, 70 ml TCl solution are added. Thirty seconds later, 37.5 ml of TCl are added. Sixty seconds later, 25 ml of chloroform are added. Three additional 25 ml aliquots of chloroform are added at 30 second intervals.

The microcapsules are recovered by centrifuging the two-phase reaction system, decanting the supernatant, and mixing the capsules with TWEEN-20 (buffered with $NaHCO_3$) and phosphate buffered saline. The capsules retain the polyvinylpyrrolidone and bovine serum albumin filler materials.

The permeability of these microcapsules may be assayed with the aid of materials of varying molecular weight, each of which are labeled with 125 Iodine. The materials used in one experiment, and their corresponding molecular weights, are listed in Table 1.

TABLE I

| BIOLOGICAL COMPOUND | MOLECULAR WEIGHT |
|---|---|
| triiodothyronine[a] | 652 |
| thyroxine[a] | 777 |
| glucagon[a] | 3,500 |
| insulin[a] | approx. 6,000 |
| parathyroid hormone[a] | approx. 9,000 |
| human growth hormone[a] | approx. 20,000 |
| tissue polypeptide antigen[b] | approx. 25,000 |

[a]Cambridge Nuclear Corp., Billerica, MA
[b]AB Sangtec Medical, Bromma, Sweden

A set of 12×75 mm polystyrene test tubes were labeled for each compound listed in Table I. Each set consisted of 7 tubes, one for each of the following time points: 5, 15, 30, 45, 60, 120, 180 and 240 minutes, plus one tube/compound for a total count of radioactivity added. One hundred microliters of an appropriate dilution of a compound was added to each of the 7 tubes; a different compound for each set. As each pre-selected time point was reached, the corresponding set of tubes for that time point, one tube/compound, were centrifuged at 2,000 xg for five (5) minutes. Following centrifugation, the supernatnant was removed by aspiration, leaving the microcapsules containing various amounts of radioactivity. For each compound, the amount of radioactivity remaining after aspiration divided by the total radioactivity added was equivalent to the fraction of the compound associated with the microcapsules. This fraction of radioactive uptake is proportional to the amount of each compound which entered the microcapsule membrane and remained with the microcapsule.

As shown in Table 2, the longer the time exposure of microcapsules to radioactive compound, the higher the percent uptake.

The experiment shows that with increasing time, more material of a particular size and weight enters the semipermeable microcapsule membrane. It also shows that the larger the size and molecular weight of the material, the lower the amount which passes across the membrane.

TABLE 2

| COMPOUND | Percent Associated with Microcapsules TIME (Minutes) | | | | | | | |
|---|---|---|---|---|---|---|---|---|
| triiodothyronine | 91.9 | 93.3 | 94.9 | 92.7 | 94.0 | 93.4 | 85.1 | 92.0 |
| thyroxine | 81.3 | 83.2 | 84.4 | 84.0 | 84.0 | 84.7 | 88.8 | 85.5 |
| glucagon | 85.1 | 83.5 | 84.3 | 84.5 | 79.2 | 77.1 | 67.7 | 67.8 |
| insulin | 75.5 | 73.6 | 73.7 | 73.9 | 73.8 | 69.0 | 73.9 | 65.6 |
| parathyroid hormone | 69.8 | 69.5 | 69.6 | 73.7 | 68.4 | 72.7 | 71.7 | 71.8 |
| human growth hormone | 34.1 | 36.0 | 38.7 | 36.1 | 36.1 | 44.2 | 46.9 | 48.0 |
| tissue polypeptide antigen | 30.8 | 32.1 | 37.3 | 37.4 | 35.1 | 39.2 | 41.5 | 44.9 |

Microcapsules made in accordance with the procedure set forth above containing, e.g., encapsulated polyvinylpryrrolidone or dextran, may be used in chromatography columns to effect the separation of various biological compounds. The utility of this separation is especially evident when applied to the chromatography of relatively small molecular weight substances, e.g., in the molecular weight range of 0–5,000 mass units.

Figure 2:
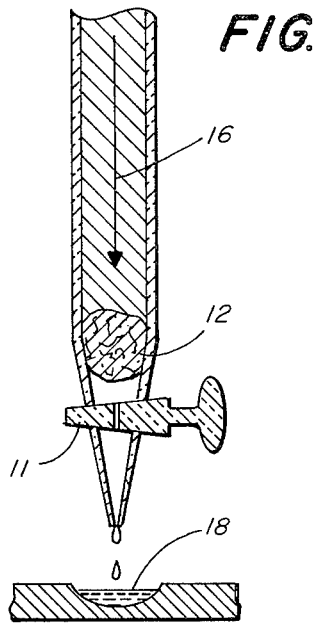
FIG. 2 is a cross-sectional view of a chromatographic column embodying the invention.

Molecular sieve separations can be done using plastic disposable chromatography columns (5 cm × 1 cm diameter) of the type generally illustrated in FIG. 2. To each column is added a suitable amount of microcapsule slurry in buffer (e.g. 0.01 M phosphate buffer, pH 7.5) to result in a 3–5 cm chromatography column. After the microcapsules have settled in the column, a solution containing various compounds to be separated is placed on the top of the bed and allowed to migrate into the microcapsule bed. A buffer is then applied to the column such that the mixture being separated is washed through the microcapsule bed. Several microcapsule bed equivalent volumes may be needed to effect complete separation of the materials.

In one experiment, a phosphate buffered saline solution containing the dye compounds fluorescein (1 mg/ml, molecular weight 376) and methylumbelliferone, (1 mg/ml, molecular weight 198), was applied to the top of a microcapsule chromatography column, as described above. After migrating into the bed, the dye mixture is separated by the microcapsules as several volumes of phosphate buffered saline are washed through the column. During passage through the column, methylumbelliferone is retained by the microcapsule to a greater extent than fluorescein, i.e, fluorescein is eluted from the column first.

This procedure demonstrates a separation of substances with low molecular weights that are fairly close together. The separation is easily followed since both materials are colored dyes and are readily visible.

EXAMPLE 2

Microcapsules are made in accordance with the procedure of Example 1 except that 1.0 ml of a solution of thyroxin antiserum (4% antibody, mw=150,000 daltons) is included in the aqueous discontinuous phase of the reaction system. The resulting capsules are formed into an approximately 3 cm × 1 cm chromatography bed. With the stopcork closed, a volume of phosphate buffered saline containing $^{125}$I-labeled thyroxin ($^{125}$I-T$_4$) and triiodothyronine (T$_3$) is loaded into the column such that the liquid level remains below the upper boundary of the microcapsule bed. After 60 minutes incubation time at 37° C., the column is drained and washed repeatedly with phosphate buffered saline (PBS). The collected solution and washings are mixed, and on assay are found to contain substantially all of the T$_3$ originally in the solution. The eluate is also substantially free of radioactivity, indicating that the $^{125}$I-T$_4$ was bound by the encapsulated T$_4$ antibody.

This procedure may be duplicated with substantially any pair of complementary substances by encapsulating the higher molecular weight substance in microcapsules having an upper limit of permeability too low to allow the passage of the encapsulated substance, but sufficient to allow passage ot its complementary, lower molecular weight component. If one or more enzymes are encapsulated, a solution of the enzyme's substrate, if contacted with the microcapsules under conditions promoting enzyme-substrate interactions, will be converted to product by the catalytic influence of the enzymes.

EXAMPLE 3

One milliliter of antibody to triiodothyronine (4% in PBS) is mixed with an equal volume of 1.2% sodium alginate in physiological saline. Next, 80 ml of a 1.5% CaCl$_2$ solution is placed in a 150 ml beaker, and stirred at a rate which induces the formation of a vortex having a conical-shaped void at its center. A glass capillary having a gradually decreasing diameter ending in a tip of inside diameter of about 50 microns is fitted with a vibrator (60 cycles per second), and the capillary tip is placed within the center of the vortex. With the vibrator turned on, the one milliliter of sodium alginate-antiserum solution is forced through the capillary with an infusion pump. Droplets on the order of 50–70 microns in diameter are thrown from the tip of the capillary and immediately enter the calcium ion solution.

After 2 to 4 minutes, when the solution is completely dispersed, the supernatant solution is removed by aspiration. The gelled capsules are then transferred to a beaker containing 1/60 of one percent polylysine (average MW 35,000 AMU) in physiological saline solution. After 2 minutes, the polylysine solution is decanted. The resulting capsules, having permanent semipermeable membranes, are then washed with physiological saline and mixed with a 0.1 percent sodium alginate solution. The capsules resist clumping and can be seen to contain a liquid core. Triiodothyronine antibody is retained within the capsules.

The microcapsules are loading into a 12 mm × 75 mm polystryrene tube, and a solution comprising $^{125}$I-T$_4$, $^{125}$I-T$_3$, and $^{125}$I$_2$ (total radioactivity equal approximately 10 microcuries) is added thereto. The capsules and solution are allowed to incubate at 37° C. for 30 minutes. On elution, the solution is found to contain about 1.0 uCi of radioactivity consisting almost totally of $^{125}$I$_2$, which rapidly passes through the column. Nine uCi of radioactivity remain in association with the microcapsules.

The microcapsules are then washed with 2 ml of PBS, and the wash solution is found to contain another 0.5 uCi of $^{125}$I$_2$.

Next, 2.0 ml of 1% bovine serum albumin (BSA) in PBS is passed through the column. Assay of the BSA solution and the microcapsules indicates that approximately 1.0 uCi of radioactivity tracable to $^{125}$I-T$_3$ remains in association with the microcapsules and 7.5 uCi ($^{125}$I-T$_4$) is present in the BSA solution.

Thus, the origional, three component solution is resolved into its respective components, and a solution of $^{125}$I-T$_4$ is produced which is substantially free of molecular iodine and T$_3$.

From the foregoing, it is apparent that the invention may be embodied in other specific forms without departing from the spirit and scope thereof. Accordingly, other embodiments are within the following claims.

What is claimed is:

1. A chromatographic device for separation of solutes of differing molecular dimensions, said device comprising, a mass of microcapsules having polymeric membranes characterized by an upper limit of permeability greater than the diameter of at least one solute to be separated, and containing a solution of a material capable of maintaining the membranes in a distended position and having a molecular weight in excess of the upper limit of permeability of said membranes said microcapsules being disposed within means defining a flow path so that said mixture of solutes may be passed therealong in contact with said microcapsulse to result in at least one zone rich in a subset of said solutes.

2. The device of claim 1 useful for separating solutes of differing molecular weights within the range of 100–5000 daltons wherein the polymeric membranes have a permeability sufficient to allow diffusion therethrough of solutes having a molecular weight of at least about 25,000 daltons.

3. The device of claim 1 wherein said material is a water soluble material.

4. The device of claim 3 wherein said material is selected from the group consisting of polyvinyl pyrrolidones, albumin, polysaccharides, polyethylene glycols, and mixture thereof.

5. The device of claim 1 wherein said means defining a flow path comprises a column.

6. A chromatographic device for affinity chromatography comprising a mass of microcapsules containing a solution of the higher molecular weight component of a pair of complementary components capable of specific binding and having polymeric membranes characterized by an upper limit of permeability sufficient to confine said higher molecular weight component but to allow diffusion of the lower molecular weight component of said pair, said membranes containing a solution of a material capable of maintaining the membranes in a distended position and having a molecular weight in excess of the upper limit of permeability of said membranes said microcapsules being disposed within means defining a flow path.

7. The device of claim 6 wherein said means defining a flow path comprises a column.

8. The device of claim 6 wherein said means defining a flow path comprises an enclosure permeable to solutes but impermeable to said microcapsules.

9. A process for separating a mixture of solutes of differing molecular dimensions, said process comprising the steps of:
passing the mixture along a flow path containing a chromatographic column including a mass of microcapsules comprising polymeric membranes having an upper limit of permeability greater than the diameter of at least one of the solutes to be separated and containing a liquid core of molecular weight above said upper limit of permeability to maintain said membrane in a distended position; and
allowing a solute in the mixture to diffuse into and out of the membranes of said microcapsules to produce a zone rich in said solute.

10. The process of claim 9 wherein said membranes have an upper permeability limit sufficient to allow diffusion therethrough of solutes having a molecular weight below about 5,000 daltons, said process being operable to resolve components of a mixture of solutes having molecular weights in the range of 100–5000 daltons.

11. The process of claim 9 wherein said microcapsules contain a material selected from the group consisting of polyvinyl pyrrolidones, polysaccharides, albumin, polyethylene glycols, and mixtures thereof.

12. A process for effecting a specific chemical change in a substrate, said process comprising the steps of
exposing the substrate to a chromatographic column of microcapsules comprising semipermeable capsule membranes having an upper limit of permeability greater than the molecular size of said substrate and containing confined enzyme in solution form, wherein said enzyme is of molecular size greater than said upper limit, said enzyme being capable of effecting the chemical change, and
allowing the substrate to traverse the capsule walls to interact with said enzyme.

* * * * *